US00PP35594P3

(12) United States Plant Patent
Leis

(10) Patent No.: US PP35,594 P3
(45) Date of Patent: Jan. 23, 2024

(54) STRAWBERRY PLANT NAMED 'CIVH725'

(50) Latin Name: ***Fragaria* x *ananassa* Duchesne ex Rozier**
Varietal Denomination: CIVH725

(71) Applicant: C.I.V.—CONSORZIO ITALIANO VIVAISTI—SOCIETÀ CONSORTILE A R.L., Comacchio FE (IT)

(72) Inventor: Michelangelo Leis, Ferrara FE (IT)

(73) Assignee: C.I.V.—CONSORZIO ITALIANO VIVAISTI—SOCIETÀ CONSORTILE A R.L., Comacchio (IT)

( * ) Notice: Subject to any disclaimer, the term of this patent is extended or adjusted under 35 U.S.C. 154(b) by 0 days.

(21) Appl. No.: 17/979,717

(22) Filed: Nov. 2, 2022

(65) Prior Publication Data

US 2023/0140848 P1 May 4, 2023

(30) Foreign Application Priority Data

Nov. 4, 2021 (QZ) ..... PBR 2021/2769

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ... A01H 5/08; A01H 5/00; A01H 6/74; A01H 6/7409
See application file for complete search history.

(56) References Cited

PUBLICATIONS

Canadian Food Inspection Agency for Aprica 2023, retrieved from the Internet at https://inspection.canada.ca/english/plaveg/pbrpov/cropreport/str/app00011242e.shtml, 4 pp. (Year: 2023).*

* cited by examiner

*Primary Examiner* — June Hwu
(74) *Attorney, Agent, or Firm* — Foley & Lardner LLP

(57) ABSTRACT

This invention relates to a new and distinct variety of strawberry plant named 'CIVH725'. The new june bearing strawberry variety named 'CIVH725' is primarily adapted to the climate and growing conditions of Northern areas and is characterized by a rustic plant, tolerant to the most common leaf and root diseases, suitable for tunnel and open field cultivation. The plant has medium-high vigour with semi-upright habit and clearly visible fruit, easy to collect; and the plant is able to have an important second flowering during the season. The new strawberry has a very high productivity, progressive and consistent during all the picking season. The fruits have conical and regular shape with red bright colour, uniform on all the fruit surface; very good resistance to handling and very good shelf-life. The flavour is very good, sweet and slightly aromatic.

4 Drawing Sheets

Latin name of the genus and species of the plant claimed: *Fragaria* x *ananassa* Duchesne ex Rozier.
Variety denomination: 'CIVH725'.

CROSS-REFERENCE TO RELATED APPLICATION

This application claims priority from Community Plant Variety Rights Application No. 2021/2769, filed Nov. 4, 2021.

BACKGROUND OF THE INVENTION

The present invention relates to a new and distinct strawberry variety named 'CIVH725'. The variety is botanically known as *Fragaria* x *ananassa* Duchesne ex Rozier.

The new strawberry 'CIVH725' is a product of a planned breeding program conducted by the inventor, Michelangelo Leis in San Giuseppe di Comacchio, Ferrara, Italy. The objective of the breeding program is to develop june bearing strawberry variety with high chill requirement, suitable both for tunnel and open field cultivation; plant with medium vigour and semi-upright habit in order to have clearly fruit easy to collect; fruit with conical, regular shape and bright red colour; skin of the fruits very resistant to handling adapted to long shelf life.

This new strawberry 'CIVH725' is a result of a controlled cross made by the inventor in 2011, in San Giuseppe di Comacchio, Ferrara, Italy. The male or pollen parent is strawberry selection designated 6C9C-007 (unpatented CIV's selection). The female or seed parent is strawberry selection designated Z6T2-060 (unpatented CIV's selection).

The new strawberry 'CIVH725' was discovered and selected by the inventor as a single flowering plant within the progeny of the stated cross in May 2013 in San Giuseppe di Comacchio, Ferrara, Italy (44° 45' North and 12° 11' East). After its selection, the new variety was asexually propagated by stolons in a nursery located in San Giuseppe di Comacchio, Ferrara, Italy. The new variety was extensively tested over the next several years in different European area with high chill condition. This propagation has demonstrated that the combination of characteristics as herein disclosed for the new cultivar are firmly fixed and retained through successive generations of asexual reproduction. The new cultivar reproduces true to type.

BRIEF SUMMARY OF THE INVENTION

'CIVH725' is primarily adapted to the climate and growing with high chill condition. This area provides the needed and correct temperatures for flower induction, and to produce a strong and vigorous plant, and to maintain fruit quality during full production.

The following traits have been repeatedly observed and are determined to be unique characteristics of 'CIVH725', which in combination distinguish this strawberry plant as a new and distinct variety:

1. Plants with semi-upright habit and medium-high vigour.
2. Adapt for tunnel and open field cultivation.
3. Fruits easy to collect.
4. Fruit with conical and regular shape during all the picking season.
5. Very good resistance to handling.
6. Good shelf life.
7. Very high productivity, progressive and consistent during all the picking season.
8. Important second flowering after the first production peak.

Plants of the new strawberry variety 'CIVH725' differ from plants of the parents, 6C9C-007 and Z6T2-060 in the characteristics described in Table 1.

TABLE 1

| Characteristic | 'CIVH725' | 6C9C-007 | Z6T2-060 |
|---|---|---|---|
| Time of ripening | Very early to early | Medium | Very early to early |
| Growth habit | Semi-upright | Upright | Semi-upright |
| Fruit size | Large | Medium | Large to very large |
| Firmness | Firm | Medium to high | Medium |

Of the many commercial cultivars known to the present inventor, the most similar in comparison to the new strawberry variety 'CIVH725' is the strawberry variety 'APRICA'. Plants of the new strawberry variety 'CIVH725' differ from plants of strawberry variety 'AFRICA' in the characteristics described in Table 2:

TABLE 2

| Characteristic | 'CIVH725' | 'APRICA' |
|---|---|---|
| Fruit: time of beginning ripening | Very early to early | Early |
| Leaf: size | Medium | Large |
| Flower: diameter | Medium to large | Large to very large |

BRIEF DESCRIPTIONS OF THE PHOTOGRAPHS

The accompanying color photographs illustrate the overall appearance of typical specimens of the new strawberry variety 'CIVH725', at various stages of development as true as it is reasonably possible with color reproductions of this type. Color in the photographs may differ slightly from the color value cited in the botanical description which accurately describe the color of 'CIVH725'. The depicted plant and plant parts of the new strawberry variety 'CIVH725' were taken in San Giuseppe di Comacchio, Ferrara, Italy, and are approximately 6 to 9 months old.

DETAILED BOTANICAL DESCRIPTION

Figure 1:
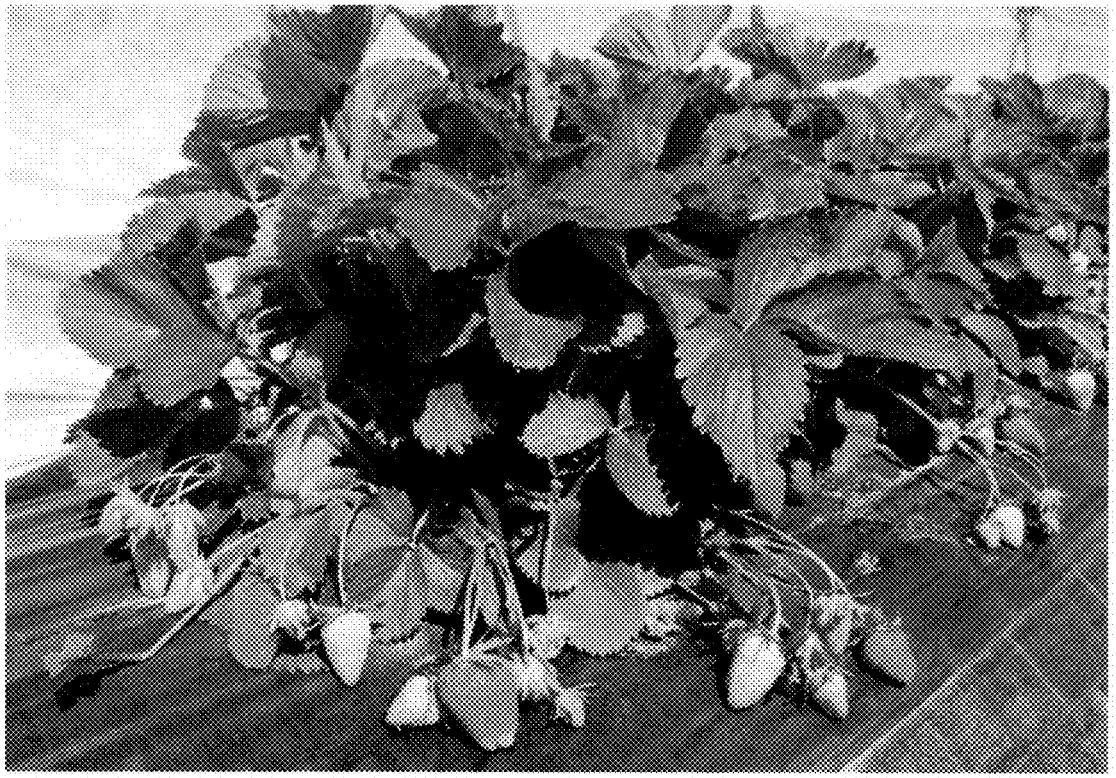
FIG. 1 shows plant of 'CIVH725'.
Figure 2:
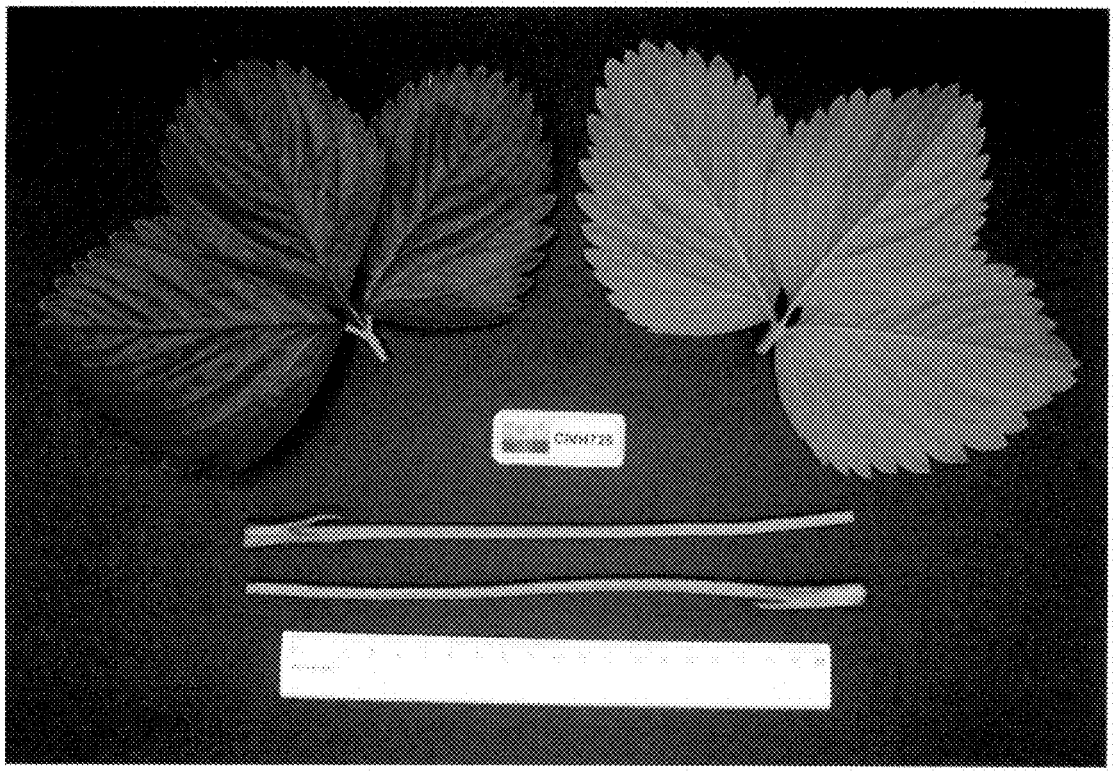
FIG. 2 shows the leaves of 'CIVH725'.
Figure 3:
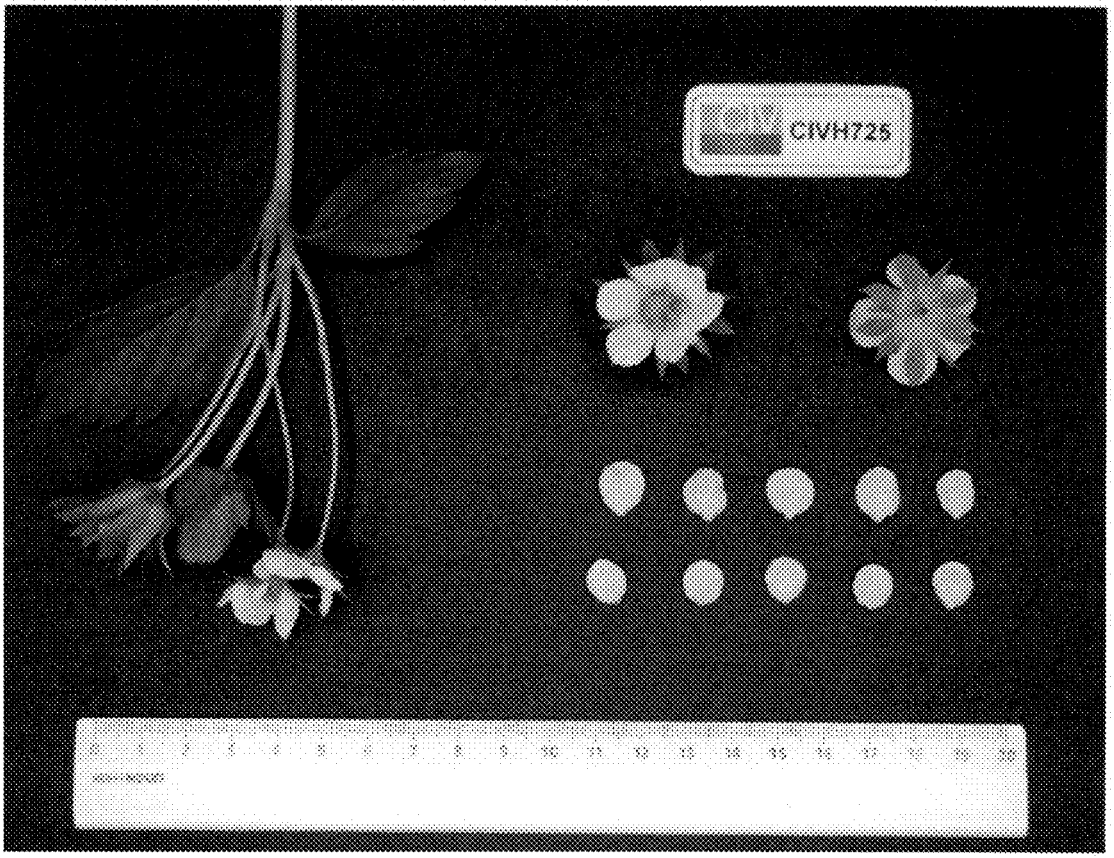
FIG. 3 shows typical flowers of 'CIVH725'.
Figure 4:
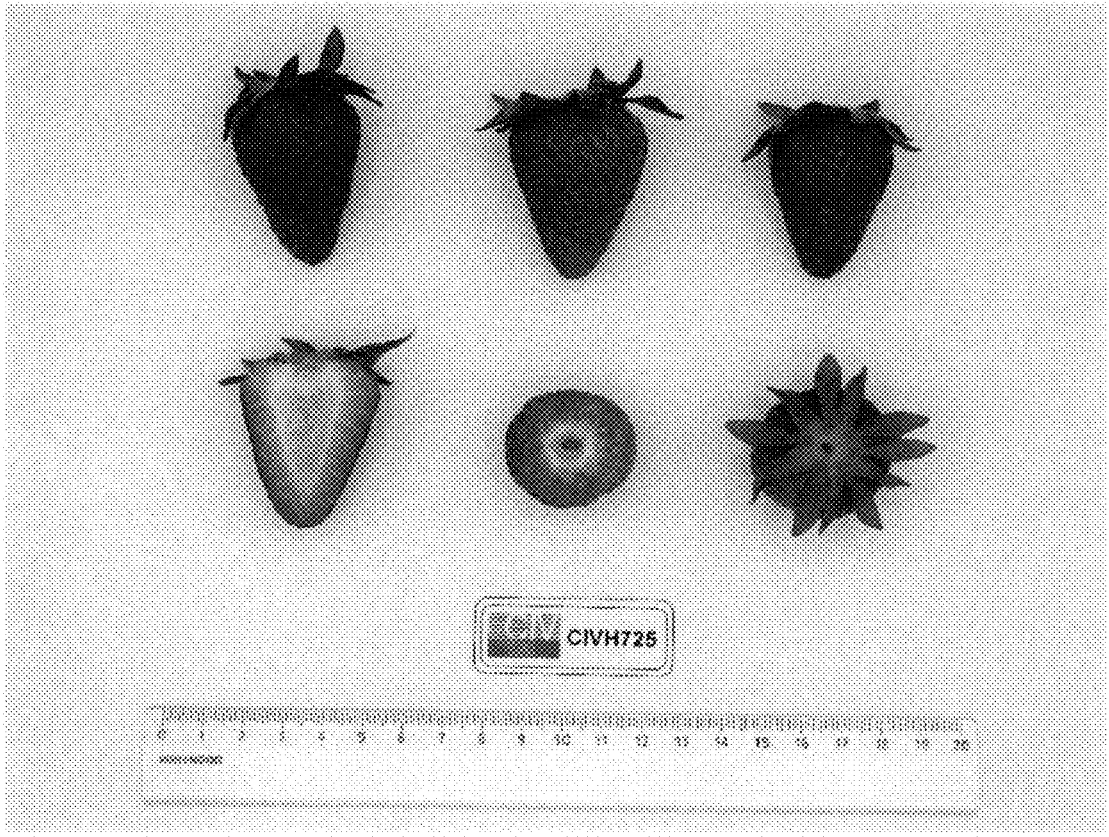
FIG. 4 shows typical fruits of 'CIVH725'.

'CIVH725' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'CIVH725', unless otherwise noted, taken during 2022 growing season in San Giuseppe di Comacchio, Ferrara, Italy. The observations, measurements and values were taken from plants of 'CIVH725' dug in December 2020 from CIV' nursery located in 44021 Codigoro, Ferrara, (locality Pomposa), Italy, and planted in July 2021 in CIV' test field in San Giuseppe di Comacchio, Ferrara, Italy.

Plants of the new strawberry variety 'CIVH725' were grown under conditions which closely approximate those generally used in commercial practice.

The observed plants were one year old plants. The plants used in the production field are produced in a nursery in CIV' nursery located in 44021 Codigoro, Ferrara, (locality Pomposa), Italy.

Yield observations and fruit quality characteristics are averaged from 3 year of data collected from the 2020 through 2022 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.), except where general colors of ordinary significance are used. Color values were taken under daylight conditions approximately in the afternoon in San Giuseppe di Comacchio, Ferrara, Italy. The approximate age of the observed plants is about 12 months.

The following tables 3-9 describe fruit, plant, stolon, foliage, fruiting truss, flower and pest/disease characteristics of the new strawberry 'CIVH725'.

TABLE 3

FRUIT CHARACTERISTICS

| Characteristic | 'CIVH725' |
|---|---|
| Color of mature fruit | Red group - RHS 46B |
| Color of internal flesh | Red group - RHS 45C |
| Color of internal core | Red group - RHS 43B |
| Length (cm) | About 4.75 cm |
| Width (cm) | About 3.1 cm |
| Ratio length/width | Moderately longer |
| Calyx diameter (cm) | About 5.3 cm |
| Average weight (gm) | About 30.5 g |
| Achene color | Yellow-green group 153B |
| Number of achenes per $cm^2$ measured at the center of berry | About 9 |

TABLE 3-continued

| FRUIT CHARACTERISTICS | |
|---|---|
| Characteristic | 'CIVH725' |
| Average weight of 1000 achenes (g) | About 0.80 g |
| Marketable yield (gm/plt) | Average 1.100 gm/plt |
| Size | Large |
| Predominant shape | Conical |
| Difference in shapes between primary and secondary fruit | Slight |
| Band without achenes | Narrow |
| Unevenness of surface | Even or slightly uneven |
| Evenness of color | Even or slightly uneven |
| Glossiness | Strong |
| Insertion of achenes | Level with surface |
| Insertion of calyx | Level with fruit |
| Attitude of the calyx | Outward |
| Size of calyx in relation to fruit diameter | Larger |
| Adherence of calyx | Strong |
| Firmness of skin | Very firm |
| Firmness of flesh | Firm |
| Distribution of red color of the flesh | Uniform |
| Hollow center expression | Medium |
| Flavor | Very good flavour, sweet and slightly aromatic |
| Soluble solids (% brix) | About 8.6% |
| Time of first and second Flowering | Early. The full bloom of first flowering is at the end of March, and the second flowering is after about 30/40 days from the first flowering in North Italy - Po Valley. |
| Time of first harvesting | Early |
| Harvest period | The first harvest period is from the beginning of May to the end of May, and the second harvest period is from the beginning of June to the end of June in North Itality - Po Valley. |
| Type of bearing | Not remontant |

TABLE 4

| PLANT CHARACTERISTICS | |
|---|---|
| Characteristic | 'CIVH725' |
| Height (cm) | About 27.5 cm |
| Spread (cm) | About 35 cm |
| Size | Small to medium |
| Habit | Semi-upright |
| Density | Medium |
| Vigor | Medium to strong |

TABLE 5

| STOLON CHARACTERISTICS | |
|---|---|
| Characteristic | 'CIVH725' |
| Average number per plant | About nr. 10-15 |
| Anthocyanin coloration | Red group - 53B |
| Anthocyanin intensity | Medium |
| Diameter at bract (mm) | About 3mm |
| Pubescence | Medium |
| Length | About 50 cm |

TABLE 6

| FOLIAGE CHARACTERISTICS | |
|---|---|
| Characteristic | 'CIVH725' |
| Foliage: | |
| Color of upper surface | Green group - 137A |
| Color of underside | Green group - 147B |
| Shape in cross section | Concave |
| Interveinal blistering | Absent or weak |
| Glossiness | Medium |
| Number of leaflets | 3 |
| Terminal Leaflet: | |
| Length (cm) | About 10.5 cm |
| Width (cm) | About 8.1 cm |
| Length/width ratio | Longer |
| Serrations/leaf | Overlapping |
| Size | Medium |
| Shape of base | Obtuse |
| Shape of teeth | Serrate |
| Petiole: | |
| Length (cm) | About 25.5 cm |
| Diameter (mm) | About 0.5 cm |
| Pubescence | Strong |
| Attitude of hairs | Outwards |
| Stipule: | |
| Length (mm) | About 4.2 cm |
| Width (mm) | About 1 cm |
| Anthocyanin coloration | Strong |
| Color | Yellow-green group 145C |

TABLE 7

| FRUITING TRUSS CHARACTERISTICS | |
|---|---|
| Characteristic | 'CIVH725' |
| Length (cm) | About 20-25 cm |
| Attitude | Erect |
| Position relative to foliage | Slightly below |
| Pubescence | Weak to medium |
| Anthocyanin intensity | Absent or very weak |
| Attitude at first pick | Horizontal |
| Number of fruit per truss | About from 4 to 6 |

TABLE 8

| FLOWER CHARACTERISTICS | |
|---|---|
| Characteristic | 'CIVH725' |
| Petal color | |
| Mature (upper) | White group - 155D |
| Mature (lower) | White group - 155D |
| Petal shape | |
| Overall | Rounded |
| Apex | Rounded |
| Base | Broad |
| Petal length (mm) | About 1 to 1.2 cm |
| Petal width (mm) | About 0.9 to 1.1 cm |
| Petal length/width ratio | Slightly longer |
| Number of petals/flower | About 5 to 6 |
| Sepals color | |
| Mature (upper) | Green group - 137A |
| Mature (lower) | Green group - 138A |

TABLE 8-continued

| FLOWER CHARACTERISTICS | |
|---|---|
| Characteristic | 'CIVH725' |
| Sepal shape | |
| Overall | Elliptic |
| Apex | Pointed |
| Base | Flat |
| Sepal length (mm) | About 0.9 to 1.1 cm |
| Sepal width (mm) | About 0.3 to 0.5 cm |
| Sepal length/width ratio | Longer |
| Number of sepals/flower | About 9 to 13 |
| Corolla diameter (mm) | About 28 mm |
| Calyx diameter (mm) | About 31 mm |
| Size of calyx relative to corolla | Larger |
| Size of inner calyx relative to outer calyx | Smaller |
| Relative position of petals | Free to touching |
| Use: Fresh market. | |
| Shipping/storage characteristics: | Very good storability and good shelf life. |

TABLE 9

| REPRODUCTIVE ORGANS | |
|---|---|
| Characteristic | 'CIVH725' |
| Receptacle color | Yellow green group - 154B |
| Pollen color | Yellow orange group - 14A |
| Stamen | Numerous with pollen present, fertile and abundant. |

TABLE 9-continued

| REPRODUCTIVE ORGANS | |
|---|---|
| Characteristic | 'CIVH725' |
| Stamen length | About 2.4 mm |
| Stamen color | Yellow-green group - 145C |
| Pollen amount | Fertile and abundant. Yellow-orange group - 14A |
| Anthers length | About 1.2 mm |
| Anthers width | About 0.8 mm |
| Anthers color | Yellow-orange group - 17C and darkening with advanced maturity. |
| Pistils | Numerous, generally average in size. |

TABLE 10

| PEST AND DISEASE REACTIONS | |
|---|---|
| Characteristic | 'CIVH725' |
| Powdery mildew (*Sphaerotheca macularis*) | Tollerant |
| Angular leaf spot (*Xanthomonas fragariae*) | Moderately susceptible |
| Botrytis fruit rot (*Botrytis cinerea*) | Very low sensibility |
| Fusarium wilt (*Fusarium oxysporum*) | Moderately susceptible |
| Anthracnose crown rot (*Colletotrichum fragariae*) | Moderately susceptible |
| Two-spotted spider mite (*Tetranychus urticae*) | Susceptible |

I claim:

1. A new and distinct strawberry plant named 'CIVH725', as herein described and illustrated by the characteristics set forth above.

* * * * *